United States Patent [19]
Tagami et al.

[11] Patent Number: 4,536,498
[45] Date of Patent: Aug. 20, 1985

[54] FUNGICIDAL COMPOSITION

[75] Inventors: Manabu Tagami, Nishinomiya; Kenzi Urayama; Tadashi Ooishi, both of Toyonaka; Yukikazu Okamoto, Ikeda; Kozo Tsuji, Nara, all of Japan

[73] Assignee: Sumitomo Chemical Company, Limited, Osaka, Japan

[21] Appl. No.: 558,829

[22] Filed: Dec. 7, 1983

[30] Foreign Application Priority Data

Dec. 15, 1982 [JP] Japan ................. 57-220966

[51] Int. Cl.$^3$ .................................. A01N 57/02
[52] U.S. Cl. ................... 514/147; 514/949; 514/975
[58] Field of Search .......................... 424/225

[56] References Cited

U.S. PATENT DOCUMENTS

| | | | |
|---|---|---|---|
| 2,927,882 | 3/1960 | Trademann et al. | 424/212 |
| 2,970,080 | 1/1961 | Oros et al. | 424/216 |
| 4,039,635 | 8/1977 | Kato et al. | 424/225 |
| 4,133,878 | 1/1979 | Gough | 424/225 |
| 4,380,537 | 4/1983 | Monroe | 424/225 |
| 4,382,077 | 5/1983 | Buchbinder | 424/225 |

FOREIGN PATENT DOCUMENTS

| | | | |
|---|---|---|---|
| 2156914 | 6/1972 | Fed. Rep. of Germany | 424/225 |
| 2196751 | 3/1974 | France | 424/225 |
| 2257598 | 8/1975 | France | 424/225 |

OTHER PUBLICATIONS

"Agricultural and Food Chemistry", vol. 10, pp. 244–248, 1962.

Primary Examiner—Albert T. Meyers
Assistant Examiner—Joyce L. Morrison
Attorney, Agent, or Firm—Stevens, Davis, Miller & Mosher

[57] ABSTRACT

A fungicidal composition containing a fungicidally effective amount of tolchlofos-methyl [O,O-dimethyl O-(2,6-dichloro-4-methylphenyl) phosphorothioate] as an active ingredient, attapulgite clay as a carrier and polypropylene glycol as a stabilizer, its formulation and its use as a fungicide.

2 Claims, No Drawings

FUNGICIDAL COMPOSITION

The present invention relates to a fungicidal composition containing a fungicidally effective amount of tolchlofos-methyl [0,0-dimethyl 0-(2,6-dichloro-4-methylphenyl)phosphorothioate] as an active ingredient, attapulgite clay as a carrier and polypropylene glycol as a stabilizer, its formulation and its use as a fungicide.

Tolchlofos-methyl is a compound having excellent controlling activity on soil plant diseases, particularly diseases caused by phytopathogens fungi belonging to Rhizoctonia genus or Corticium genus. When this compound is used as an active ingredient of fungicides, it is generally formulated into various compositions such as wettable powder, dust, granule, emulsifiable concentrate, suspension concentrate and the like by mixing with solid or liquid carriers, surface active agents and other auxiliaries for formulation. Attapulgite clay, one of solid carriers, is superior in performances required for carriers such as oil-absorbing ability, dispersibility in water, suspension stability, etc., and besides economically cheap, but the solid compositions such as wettable powder, dust, granule, etc. of tolchlofos-methyl as an active ingredient containing attapulgite clay as a carrier could not be put to practical use in terms of composition stability.

The present inventors, as a result of an extensive study on the stabilization of the solid compositions of tolchlofos-methyl as an active ingredient, particularly wettable powder, dust granule containing attapulgite clay as a carrier, found that a stable solid composition is obtained by adding polypropylene glycol as a stabilizer.

Attapulgite clay is palygorskite type clay with magnesium aluminum silicate as a main component and easily available as fine powder and granule having various particle size distributions. The granular attapulgite has particularly high oil-absorbing ability, so that even solid active ingredients like tolchlofos-methyl can be formulated to the composition very easily and economically by merely dissolving or dispersing them in a nonvolatile solvent in order to attain mixing and impregnation.

There are many kinds of polypropylene glycol ranging from low molecular weight ones to high molecular weight ones. But, those having a molecular weight less than 400 are not suitable in terms of stabilization, and also those having a molecular weight more than 6000, because of their high viscosity, are not suitable in terms of easy formulation.

The fungicidal composition of the present invention contains from 1 to 70 parts by weight of tolchlofos-methyl as an active ingredient and from 5 to 40 parts by weight of polypropylene gylcol (from 10 to 60%, preferably from 30 to 50% based on attapulgite clay), the rest being attapulgite clay. As need arises, however, various kinds of auxiliaries for formulation such as surface active agents, machine oil, liquid paraffin, animal or vegetable oil, etc. may be added, and solid carrier such as kaolin clay, talc, calcite, diatomaceous earth, synthetic hydrated silicon dioxide, etc. may be used in combination with attapulgite clay.

The fungicidal composition of the present invention can be formulated by the usual formulation method without using any special equipments and apparatus. That is, said composition is well obtained by finely pulverizing the active ingredient in advance by a hammer mill, etc. with addition of auxiliaries for pulveration if necessary, mixing the resulting pulverized mixture with attapulgite clay in a ribbon mixer, Nauta mixer or the like, and then adding polypropylene glycol, followed by mixing and impregnation; by mixing the finely pulverized active ingredient with polypropylene glycol to obtain a dispersion which is then mixed with attapulgite clay, followed by impregnation, or by wet-milling a mixture of the active ingredient and polypropylene glycol by a colloid mill, attrition mill, sand mill or the like, followed by mixing with attapulgite clay and impregnation.

The fungicidal composition of the present invention will be illustrated with reference to the following Examples. Parts in the Examples are by weight.

EXAMPLE 1

5.0 Parts of tolchlofos-methyl and 0.5 part of synthetic hydrated silicon dioxide were mixed in a ribbon mixer, finely pulverized by a hammer mill and mixed with 30.0 parts of polypropylene glycol having an average molecular weight of 1000, followed by dispersion. The dispersion thus obtained was added to 64.5 parts of attapulgite clay (Attapulgus clay ALVM 30/60, supplied from Engelhard Minerals & Chemicals Co.) in a Nauta mixer with stirring, followed by mixing and impregnation. Thus, a 5% granule of tolchlofos-methyl was obtained.

EXAMPLE 2

50.0 Parts of tolchlofos-methyl and 5.0 parts of synthetic hydrated silicon dioxide were mixed and finely pulverized. The pulverized mixture was then mixed with 2.0 parts of polyoxyethylene alkylarly sulfate (Sorpol 5073, produced by Toho Kagaku Co.), 2.0 parts of sodium lignosulfonate and 29.0 parts of attapulgite clay [Attapulgus clay fine powder (average particle diameter, 18 $\mu$m), supplied from Engelhard Minerals & Chemicals Co.] in the Henschel mixer at a revolution speed of 700 rpm. To the mixture thus obtained was added 12.0 parts of polypropylene glycol having an average molecular weight of 750, followed by mixing and impregnation. Thus, a 50% wettable powder of tolchlofos-methyl was obtained.

EXAMPLE 3

10.0 Parts of tolchlofos-methyl and 29.0 parts of polypropylene glycol having an average molecular weight of 2000 were mixed and wet-milled by a colloid mill. Thereafter, the mixture obtained was added to 61.0 parts of attapulgite clay (Attapulgus clay AARVM 20/50, supplied from Engelhard Minerals & Chemicals Co.) in a Nauta mixer with stirring, followed by mixing and impregnation. Thus, a 10% granule of tolchlofos-methyl was obtained.

EXAMPLE 4

2.5 Parts of tolchlofos-methyl and 0.25 part of synthetic hydrated silicon dioxide were mixed and finely pulverized, and the pulverized mixture was then mixed with 74.25 parts of attapulgite clay [Attapulgus clay fine powder (average particle diameter, 18 $\mu$m), supplied from Engelhard Minerals & Chemicals Co.] in the Henschel mixer set at a revolution speed of 700 rpm. To the mixture thus obtained was added 23.0 parts of polypropylene glycol having an average molecular weight of 1000, followed by mixing and impregnation. Thus, a 2.5% dust of tolchlofos-methyl was obtained.

The fungicidal compositions of the present invention will be compared with those of the following Comparative Examples. Parts in the Comparative Examples are by weight.

Comparative Examples 1, 2 and 3

A granule containing 5% of tolchlofos-methyl was obtained in the same manner as in Example 1 but using polyethylene glycol having an average molecular weight of 600, dipropylene glycol and machine oil in place of polypropylene glycol having an average molecular weight of 1000.

Comparative Example 4

A granule containing 5% of tolchlofos-methyl was obtained by dispersing 5.5 parts of the finely pulverized product used in Example 1 in water, and impregnating 94.5 parts of attapulgite clay with the dispersion obtained above in the same manner as in Example 1, followed by drying at 60° C. for 2 hours.

Comparative Example 5

A wettable powder containing 50% of tolchlofos-methyl was obtained in the same manner as in Example 2 except that polypropylene glycol having an average molecular weight of 750 was not used and 41.0 parts of attapulgite clay was used.

The composition stability and fungicidal activity of the fungicidal composition of the present invention will be illustrated with reference to the following Test Examples of accelerating test and biological controlling activity test.

Test Example 1

Accelerating test

Ten grams each of the compositions obtained in Examples 1, 2, 3 and 4 and Comparative Examples 1, 2, 3, 4 and 5 was placed in a 50-ml glass bottle and sealed tightly. The compositions were stored in a constant-temperature apparatus of 40° C. for 3 months or in the same apparatus of 60° C. for 1 month, and then the amount of active ingredient was determined by gas chromatography. The results are shown in Table 1.

In the above gas chromatography, the active ingredient was extracted with acetone and the amount was determined by a gas chromatograph equipped with a hydrogen flame ionization detector (F.I.D.) according to the internal standard method.

TABLE 1

| Test composition | Stabilizer | Content of active ingredient (%) Storage for 40° C. × 3 months | Storage for 60° C. × 1 months |
|---|---|---|---|
| 5% Granule of Example 1 | Polypropylene glycol (average molecular weight, 1000) | 4.86 | 4.86 |
| 5% Granule of Comparative Example 1 | Polyethylene glycol (average molecular weight, 600) | 3.40 | 3.23 |
| 5% Granule of Comparative Example 2 | Dipropylene glycol | 3.44 | 3.50 |
| 5% Granule of Comparative Example 3 | Machine oil | 2.65 | 2.36 |
| 5% Granule of Comparative Example 4 | None | 1.04 | 0.90 |
| 50% Wettable powder of Example 2 | Polypropylene glycol (average molecular weight, 750) | 49.5 | 49.0 |
| 50% Wettable powder of Comparative Example 5 | None | 35.4 | 32.2 |
| 10% Granule of Example 3 | Polypropylene glycol (average molecular weight, 2000) | 9.85 | 9.73 |
| 2.5% Dust of Example 4 | Polypropylene glycol (average molecular weight, 1000) | 2.48 | 2.45 |

Test Example 2

Biological controlling activity test on damping-off of cucumber (*Rhizoctonia solani*)

Plastic pots were filled with field soil and infested soil with cultured *Rhizoctonia solani*, and the surface soil of the pots was well mixed with prescribed amount of the granule obtained in Example 1 and Comparative Examples 1, 2, 3 and 4. Thereafter, the seed of cucumber (var., Shimoshirazu-jihai) was sowed at a rate of 10/pot and covered with soil. After two weeks' cultivation in a greenhouse, the infectious state was examined and the percentage of healthy seedlings was calculated from the following equation.

$$\text{Percentage of healthy seedlings (\%)} = \frac{\text{Number of healthy seedlings in each treated plot}}{\text{Number of healthy seedlings in untreated and uninoculated plot}} \times 100$$

The results are shown in Table 2.

TABLE 2

| Test composition | Stabilizer | Dosage rate of active ingredient (kg/10 ares) | Percentage of healthy seedlings (%) | Phyto-toxicity |
|---|---|---|---|---|
| 5% Granule of Example 1 | Polypropylene glycol (average molecular weight, 1000) | 1.0 | 100.0 | — |
| 5% Granule of Comparative Example 1 | Polyethylene glycol (average molecular weight, 600) | " | 63.3 | — |
| 5% Granule of Comparative Example 2 | Dipropylene glycol | " | 70.0 | — |
| 5% Granule of Comparative Example 3 | Machine oil | " | 53.3 | — |
| 5% Granule of Comparative | None | " | 43.3 | — |

TABLE 2-continued

| Test composition | Stabilizer | Dosage rate of active ingredient (kg/10 ares) | Percentage of healthy seedlings (%) | Phytotoxicity |
|---|---|---|---|---|
| Example 4 Inoculated and untreated plot | — | — | 0.0 | — |
| Uninoculated and untreated plot | — | — | 100.0 | — |

Test Example 3

Biological controlling activity test on southern blight of kidney bean (*Corticium rolfsii*)

Plastic pots were filled with field soil and infested soil with cultured *Corticium rolfsii*, and a prescribed amount of the wettable powder obtained in Example 2 and Comparative Example 5 was diluted with water and applied to the soil of the pots. Thereafter, the seed of kidney bean (var. Nagauzura) was sowed at a rate of 10/pot and covered with soil. After three weeks' cultivation in a greenhouse, the infectious state was examined and the percentage of healthy seedlings was calculated from the following equation:

$$\text{Percentage of healthy seedlings (\%)} = \frac{\text{Number of healthy seedlings in each treated plot}}{\text{Number of healthy seedlings in untreated and uninoculated plot}} \times 100$$

The results are shown in Table 3.

TABLE 3

| Test composition | Stabilizer | Dosage rate of active ingredient (kg/10 ares) | Percentage of healthy seedlings (%) | Phytotoxicity |
|---|---|---|---|---|
| 50% Wettable powder of Example 2 | Polypropylene glycol (average molecular weight, 750) | 1.0 | 100.0 | — |
| 50% Wettable powder of Comparative Example 5 | None | " | 46.7 | — |
| Inoculated and untreated plot | — | — | 3.3 | — |
| Uninoculated and untreated plot | — | — | 100.0 | — |

What is claimed is:

1. A fungicidal composition which comprises 1–70 parts of tolchlofos-methyl as an active ingredient, 5–40 parts of polypropylene glycol having a molecular weight from 400 to 6,000 as a stabilizer, and as the sole carrier the remainder of the composition being attapulgite clay, wherein the amount of said polypropylene glycol is from 10 to 60% by weight of the amount of attapulgite clay.

2. A method for controlling a phytopathogenic fungi belonging to the Rhizoctonia or Corticium genus which comprises applying an effective amount of the composition according to claim 1, to the phytopathogenic fungi.

* * * * *